United States Patent [19]

Kohn

[11] 4,048,324

[45] Sept. 13, 1977

[54] FUNGICIDAL COMPOSITION AND METHOD

[76] Inventor: Armand Kohn, 5, Avenue Foch, 92 Garches, France

[21] Appl. No.: 536,159

[22] Filed: Dec. 24, 1974

[30] Foreign Application Priority Data

June 10, 1974 France .................................. 74.19891
Dec. 28, 1973 France .................................. 73.46835

[51] Int. Cl.$^2$ .......................................... A01N 11/04
[52] U.S. Cl. ................................ 424/294; 260/438.1; 424/287; 424/289; 424/293
[58] Field of Search .......................... 260/438.1, 429.9; 424/289, 294

[56] References Cited

U.S. PATENT DOCUMENTS

| | | | |
|---|---|---|---|
| 2,455,687 | 12/1948 | Liberthson | 260/438.1 |
| 2,557,172 | 6/1951 | Brooks | 424/270 X |
| 2,686,798 | 8/1954 | Gmitter | 260/438.1 X |
| 2,700,683 | 1/1955 | Tesoro et al. | 424/329 X |
| 2,700,684 | 1/1955 | Tesoro et al. | 424/329 X |
| 2,805,996 | 9/1957 | Deger | 260/438.1 X |
| 2,878,155 | 3/1959 | Cruickshank | 260/438.1 X |
| 2,883,426 | 4/1959 | Brackman | 260/438.1 X |
| 2,902,401 | 9/1959 | Harwood | 260/438.1 X |
| 2,924,551 | 2/1960 | Harwood | 260/438.1 X |
| 2,924,552 | 2/1960 | Harwood | 260/438.1 X |
| 2,928,856 | 3/1960 | Harwood | 260/438.1 X |
| 2,977,279 | 3/1961 | Kosmin | 260/438.1 X |
| 3,351,647 | 11/1967 | Butler et al. | 260/438.1 X |
| 3,914,266 | 10/1975 | Hay | 260/438.1 |

FOREIGN PATENT DOCUMENTS 1,130,117  1/1957  France

*Primary Examiner*—Helen M. S. Sneed
*Attorney, Agent, or Firm*—Ostrolenk, Faber, Gerb & Soffen

[57] ABSTRACT

An improved fungicidal and fungistatic composition has been achieved, which does not stain plants, has neither phytotoxic effect nor toxicity to animals at concentrations required for controlling fungi development, and is biodegradable in soil. The composition is a mixture of copper salt or hydroxide with an aliphatic amine or polyamine having at least 8 carbon atoms and 1 to 4 secondary or/and tertiary amine functions; the molecule of the amine contains a $C_4$ to $C_{18}$ alkyl attached to one nitrogen atom and at least one further heavy group, such as $C_4$ to $C_{18}$ alkyl or $(CH_2)_q$—COOH ($q$ being 1 to 3) attached to nitrogen atom or atoms of the amine. The composition contains a complex of copper with the amine. Preferably the presence of halogens, $NO_2$ and $SO_3$ in the cupric salt is avoided. The composition is effective against many species of fungi and particularly against oidium. Particularly active compositions contain quaternary ammonium compounds which act synergistically with the copper-amine combination.

24 Claims, No Drawings

FUNGICIDAL COMPOSITION AND METHOD

This invention concerns a new fungicidal and fungistatic composition; it more especially relates to a composition containing certain particular amine-copper complexes.

BACKGROUND OF THE INVENTION

Fungicides play an important role in; agriculture, because without their use a considerable part of vegetable, fruit, cereals and flowers crop would be lost every year. The disinfection of all kinds of buildings, containers and tools require also the application of fungicides to avoid disease, moulds growing, contamination of foods and so on. On the other hand, in view of the specificity of most of the known fungicidal substances, and in view of the great number of existing fungi, it is not surprising that hundreds of various fungicides are commercially available. Generally speaking each of the commercial products has utility in a certain field and to a certain extent: that means almost each product is suitable for killing certain species of moulds, on certain plants or materials, and in certain conditions of temperature, light, humidity etc. Nevertheless, much is still to be improved, particularly as concerns toxicity, phytotoxicity, biodegradability, staining and killing some very virulent widespread germs.

In the course of last 20 years, attractive attempts have been made to improve the fungicidal action of copper. As known, copper compounds have been used with success, particularly in the protection of vine against mildew, for almost a century; however, as the composition must be substantially neutral, it bears copper in the form of hydroxide, basic sulfate, oxychloride or similar water insoluble material; the slurry, such as the known Bordeaux mixture, sprayed onto the plants must have a rather high content in Cu, generally about 5 g Cu per liter, to be effective. Thus considerable amounts of copper are sprayed every year onto fields and some of the insoluble compound remains stuck to fruit. The improvement, which has been proposed by several authors since 1955, consists in using copper in/the form of its complexes with amines. Since numerous of the complexes being water soluble and highly active against fungi, they are effective in much lower dose than are the old insoluble compounds.

Thus, French Pat. No. 1,130,117 suggests on page 2, lines 1-10, the use of metal complexes of polyamines such as lauryl-ethylene-diamine or tetraethylene-pentamine. U.S. Pat. No. 2,924,551 teaches the application of fungicides constituted by copper or other heavy metals complexes with diamines R'R'N(CH$_2$)$_n$NRR', where R is an aliphatic hydrocarbon C$_8$ to C$_{20}$ radical, $n$ is 2 to 5, and R' is methyl or H, at least one of the R' present being H. According to French Pat. No. 1,301,904, the complexes of the above U.S. Patent are too phytotoxic and should be replaced by complexes derived from the particular polyamines represented by the formula:

RNH(CH$_2$)$_3$NH(CH$_2$)$_3$NHR' where R is a C$_6$ to C$_{22}$ aliphatic hydrocarbyl, while R' is H or a group —CH$_2$CH$_2$CH$_2$NH$_2$.

U.S. Pat. No. 2,977,279 discloses fungicides formed by copper complexes with N-alkenyl-alkylene-polyamines having 3 to 5 amino groups separated by —CH$_2$CH$_2$— or —CH$_2$CH$_2$CH$_2$— chains; the alkenyl radical on N has 8 to 18 C atoms.

As a matter of fact, most of the above amino-copper complexes are quite active anticryptogamic agents and several of them strongly kill various fungi. Their use results in a very substantial sparing of copper, as solutions having 0.2 to 0.5 g Cu per liter are at least as effective as conventional copper compounds slurries with 5 g Cu/l, while amino-copper complex solutions of 0.5 to 1 g Cu/l are much more active than the slurries. The question arises why the copper amino complexes have had no commercial success until now. It seems the answer to this question is found in the third paragraph of page 1 of the above mentioned French Pat. No. 1,301,904, which points out the phytotoxicity of the complexes disclosed in U.S. Pat. No. 2,924,551. Thorough experiences showed that, in fact, not only were the complexes of U.S. Pat. No. 2,924,551 were too much dangerous in practice, but also those of the other prior art cited, including those of the French Pat. No. 1,301,904 itself.

To best understand the matter it will be useful to consider Table I, columns 5 and 6, of the U.S. Pat. No. 2,924,551. It is true that the lethal doses LD$_{50}$ of the Cu complexes concerned, versus the studied fungi are 0.6 to 14.0 ppm. as shown in the 6th vertical column of the Table, when determined in vitro by the "Standard Fungicidal Test" of Am. Phys. Soc. It is also true the minimal phytotoxic dosage on tomato or pepper, in certain particular conditions, may be 2,000 ppm. However, in field experience to obtain significant results one must spray a solution or emulsion of amine Cu complex at a concentration of at least 1000 ppm. and often even as high as about 3000 ppm. This practice is the same as with all conventional fungicides. For instance, it is known that according to the Standard Fungicidal Test maneb (manganese ethylene-bis-dithiocarbamate) exerts a fungistatic action at a dosage of about 10 ppm; nevertheless in practice concentrations of 1000 to 2800 ppm are recommended in producers pamphlets as well as in phytotechnical literature ("Chemical and Natural Control of Pests" — E. R. de ONG — Reihold Publishing Corp. — 1960; page 134 second paragraph: 2 pounds of 70% maneb per 100 gallons i.e. 1670 ppm.). That means when the Cu complexes are used in practice, the necessary concentration is of the same order of magnitude as the minimal phytotoxic dosage. Then it is not surprising that risks of damage to plants occur.

On the other hand, the sensitivity of different vegetals to chemical compounds strongly varies with the specie of plant, age, temperature, air humidity, intensity of light etc. It is not possible to generally characterize the phytotoxicity of a compound by tests on one or two plants. While tomato or pepper may resist, for example, 1500 ppm of a Cu-amine complex, grape or vetch can be less or more severely attacked. That is the reason for which the toxicity to plants of the compositions according to the present invention was tested on a great number of various plants, in summer, under several hours of sunning per day, and average statistical data were drawn from the tests.

BRIEF DESCRIPTION OF THE INVENTION

According to the present invention, fungicidal compositions are made with amine copper complexes which do not exhibit the above discussed drawbacks. The new compositions are harmless to most of plants in normal conditions, and they may be used at the concentrations practically required for destroying a great number of cryptogamic and microbial pests. The main active materials of the compositions bear the advantage of being biodegradable and of playing even the role of fertilizer when degraded in soil. The active material is constituted by a combination of a copper II compound with an aliphatic mono- or poly-amine, having no primary amine functions bearing a heavy alkyl or alkenyl radical on its chain end nitrogen and having, in addition, at least one second rather heavy substituent which may be a further amine bearing a heavy alkyl or carboxyl group.

DETAILED DESCRIPTION OF THE INVENTION

The invention results from the unexpected finding that the toxicity to insects and mammals, as well as the phytoxicity of amine copper complexes may be considerably reduced by introducing into the amine moiety certain substitution groups; a further surprising fact is that while the above toxicity and phytotoxicity strongly decreases the fungistatic and fungicide power of the complex increases; moreover antibacterial action is improved by the introduction of the particular groups.

The new composition according to the invention comprises essentially one or several aliphatic linear amines having each at least 8 carbon atoms and 1 to 4 secondary or/and tertiary amine functions, while there are in the molecule of the amine, attached to nitrogen, at least two rather heavy groups one of which is a $C_4$ to $C_{18}$ alkyl or alkenyl and the other or others are selected from the group consisting of $C_4$ to $C_{18}$ alkyls and alkenyls and $-(CH_2)_q-COOH$ groupings in which $q$ is 1 to 3. The composition further comprises cupric hydroxide or a cupric salt the anion of which is not noxious to plants, at least a part of the copper present being combined with the amine in the form of complex. There are 0.1 to 10 atoms of amine nitrogen for each Cu atom in the composition and more often 0.25 to 4 atoms N for 1 Cu.

The composition may advantageously contain various additives enhancing the pesticidal action of the amine-Cu combination or improving its contact, spreading or absorption by leaves. Such suitable additives are particularly quaternary ammonium compounds, alkylsulfoxides, polyols, certain amides as diethylformamide or hexamethyl-phosphotriamide.

With respect to known copper complexes fungicides, the above definition will be better understood when considering for instance the amines of examples 1 and 2 of U.S. Pat. No. 2,924,551. The amine

$C_{12}H_{25}-NH-CH_2CH_2CH_2-NH_2$ (example 1)

when used in field experiments, shows harmful to several plants, particularly in summer; but it suffices to replace it by a homologous secondary amine according to the present invention,

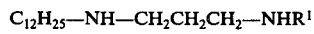
$C_{12}H_{25}-NH-CH_2CH_2CH_2-NHR^1$ where $R^1$ is $-C_4H_9$ to $-C_{18}H_{37}$ and particularly $-C_6H_{13}$ to $-C_{12}H_{25}$; that means substituting the H of $-NH_2$ with a second heavy alkyl, to obtain a very suitable composition. Another way according to the present invention is to take a corresponding amino-acid in which $R^1$ is $-CH_2COOH$, $-CH_2CH_2COOH$ or $-CH_2CH_2CH_2COOH$, for example:

$C_{12}H_{25}-NH-CH_{hd\ 2}CH_2CH_2NH-2COOH$.

Similarly in the example 2 of the U.S. Patent concerned, in the amine

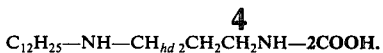
$C_{13}H_{27}-NH-CH_2CH_2CH_2-N\begin{smallmatrix}CH_3\\CH_3\end{smallmatrix}$ the two $-CH_3$ of the tertiary nitrogen present are insufficient to correct phytotoxicity, while . . . $-NH-C_6H_{13}$,

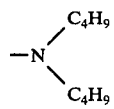
$-N\begin{smallmatrix}C_4H_9\\C_4H_9\end{smallmatrix}$ or $-NH-CH_2COOH$ in place of

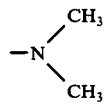
$-N\begin{smallmatrix}CH_3\\CH_3\end{smallmatrix}$ leads to excellent compositions.

On the other hand, an aqueous solution having 1200 ppm of the N-(tetrapropenyl)-diethylene-triamine copper II complex, described in examples 1 by 5 of U.S. Pat. No. 2,977,279, has been found harmful to vine, lilac and soya-bean, while being inoffensive to tomato. When the amine of this complex, i.e.

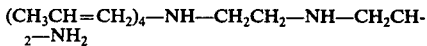
$(CH_3CH=CH_2)_4-NH-CH_2CH_2-NH-CH_2CH_2-NH_2$ is replaced by

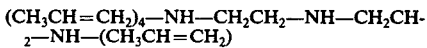
$(CH_3CH=CH_2)_4-NH-CH_2CH_2-NH-CH_2CH_2-NH-(CH_3CH=CH_2)$ according to the present invention, there is no longer phytotoxicity to the above mentioned plants.

The amines of the compositions according to the invention may be aliphatic amines having no primary amine function and bearing at least two heavy alkyls or alkenyls on nitrogen atom or atoms, or aliphatic aminoacids the chain end amine function of which is substituted with a heavy alkyl, or alkenyl.

All these compounds can be schematically represented by the general formula

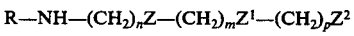
$R-NH-(CH_2)_nZ-(CH_2)_mZ^1-(CH_2)_pZ^2$ where R is an alkyl or alkenyl having 4 to 18 carbon atoms, each of the symbols Z, $Z^1$ and $Z^2$, identical or different, may be

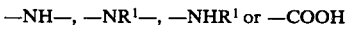
$-NH-, -NR^1-, -NHR^1$ or $-COOH$ $R^1$ being a $C_4$ to $C_{18}$ alkyl or alkenyl or $-(CH_2)_q-COOH$ with $q=1$ to 4; $n$ is an integer of 1 to 6 and more often than not 1 to 3; $m$ and $p$ are integers of 0 to 6, more generally 0 to 3. It is understood $Z^1$ or/and $Z^2$ do not exist when respectively $m$ or/and $p$ are zero.

One or several of the $-CH_2-$ chains may be branched by alkyl radicals, more particularly lower alkyls; preferably there is no more than one such branching in each of the —CH$_2$— chains; at best the total number of the branching alkyls is 0 to 3 in the amine molecule. The concerned part of the molecule has then for example the structure:

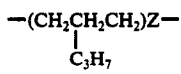

According to the above representation the amine used has only 1 to 4 amine nitrogen atoms, and at most three —COOH groupings. Indeed amines of longer chains, e.g. amines having more than 4N, for example 5 or 6, as well as amino-acids with more than 3COOH could be used, but such compounds generally give very viscous or hard products with copper salts, and thus are not easy to work. On the other hand, they are commercially not as available as the compounds of the above formula are.

Here are some non limitative examples of the substituted amines suitable for the preparation of compositions according to the invention.

N,N'-di-n-hexyl-diamino-methane
N,N'-di-n-hexyl-1,2-diamino-ethane,
N-decyl-N'-butyl-1,2-diamino-ethane,
N,N'-diheptyl-1,3-diamino-propane,C$_7$H$_{15}$—N-H—CH$_2$CH$_2$CH$_2$—NH—C$_7$H-,
N,N-dibutyl-N'-butyl-1,3-diamino-propane,
N-oleyl-N'-hexyl-1,3-diamino-propane,
N,N'-dioctyl-1,3-diamino-1-methyl-propane

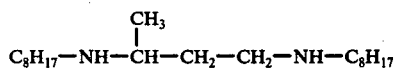

N,N''-dilauryl-diethylene-triamine,
N,N',N''-trihexyl-diethylene-triamine:

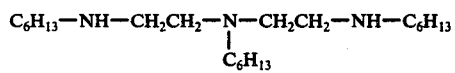

N,N''-dioctyl-diethylene-triamine,
N,N',N''-trioctyl-diethylene-triamine,
N,N'''-dihexadecyl-dipropylene-triamine,
N,N'-dilauryl-tetramethylene-1,4-diamine,
C$_{12}$H$_{25}$—NH—CH$_2$CH$_2$CH$_2$CH$_2$—NH—C$_{12}$H$_{25}$,
N,N'''-dibutyl-triethylene-tetramine, C$_4$H$_9$—N-H—CH$_2$CH$_2$—NH—CH$_2$CH$_2$—NH—CH$_2$CH$_2$—NH—C$_4$H$_9$, Commercially available products are generally formed by mixtures of several homologous amines bearing different alkyls or alkenyls R and R$^1$ which originate from natural oils or fats, such as coco-nut, olive, linseed, peanut, castor and other oils, or lard, spermaceti, tallow butter etc. which serve as starting materials in the production of the amines. The number of carbon atoms in the different R and R$^1$ of the mixture varies generally between 8 and 18, while certain numbers are predominant: thus, for example, in materials originating from coco-nut there is more than 50% C$_{12}$ and only a few percent of C$_8$ and C$_{18}$; when the material comes from tallow, C$_{18}$ (oleic) exceeds 40% while the content in C$_{12}$ is very low.

Illustrative non limitative examples of the above amines, in which R and R$^1$ are alkenyls, are such as:
N,N'-dihexenyl-diamino-methane,
N-decenyl-N'-butenyl-1,2-diamino-ethane,
N,N'-di-dodecenyl-ethylene-diamine
N,N''-(tripropenyl)-diethylene-triamine
N,N'-(di-isobutenyl)-ethylene-diamine
N,N''-di-octenyl-diethylene-triamine
N,N',N''-tri-octenyl-diethylene-triamine
N-oleyl-N''-butenyl-dipropylene-triamine
N-oleyl-N',N''-dibutenyl-dipropylene-triamine, etc.

Generally the alkenyl-alkylene polyamines recited in columns 3 and 4 of U.S. Pat. No. 2,977,279 can be transformed into amines usable in the present invention, by substituting the second H of their primary amine function with an alkyl or alkenyl having 4 to 18 carbon atoms or with the above defined grouping —(CH$_2$)$_q$—COOH. It is also useful to introduce a third or fourth substituent to create an N,N',N'' or N,N',N'',N''' substituted amine, as above exemplified.

The amines preferred for the preparation of the compositions according to the invention are those in which R and R$^1$ are at least C$_6$, because with such substituents the material is surface active; this bears great advantage for the pesticide effect of the material, and generally when amine is surface active, its copper complex shows the same property even if there is an excess of copper salt.

All the above defined amines may be used, in the composition according to the invention, as such or in the form of their salts, preferably those of the anions preferred, as above explained. Thus, acetates, propionates, lactates, phosphates are good examples of the amines salts usable.

When one or several of the amine-substituents, according to the invention, are carboxyl bearing chains, the compound is an amino-acid such as

or

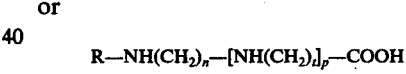

where R, $n$ and $p$ have the same meaning as above, while $t$ is an integer of 1 to 6, preferably 1 to 3. On one, or more, of the —NH— groups the H atom may be replaced by a grouping —(CH$_2$)$_q$—COOH q being 1 3. While R may be C$_4$ to C$_{18}$, it is preferably constituted by an alkyl or alkenyl having at least 6 carbon atoms, and still better 8 to 18C, because then the amino-acide exhibits a quite strong surface action which is very advantageous to its use in pesticide compositions.

Commercially available surface active amino-acids are generally formed by mixtures of several homologous amino-acids having different alkyls or alkenyls R which originate from natural oils or fats, as above pointed out concerning the corresponding amines.

Here are some non limitative examples of amino-acids available, suitable to the compositions of the invention.
R—NH—CH$_2$COOH — alkyl-amino-acetic acid,
R—NHCH$_2$CH$_2$COOH — alkyl-amino propionic acid)("AMPHORAM").
R—NHCH$_2$CH$_2$CH$_2$NHCH$_2$CH$_2$COOH — alkyl-propylene-diamino propionic acid ("DIAMPHORAM").
R—(NHCH$_2$CH$_2$CH$_2$)$_2$NHCH$_2$CH$_2$COOH — alkyl-dipropylene-triamino-propionic acid ("TRIAMPHORAM").

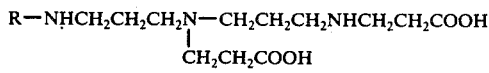

alkyl-dipropylene-triamino dipropionic acid (TRIAMPHORAM).
R—(NHCH₂CH₂CH₂)₃NHCH₂CH₂COOH—alkyl-tripropylene-tetramino Propionic acid ("POLYAMPHORAM").

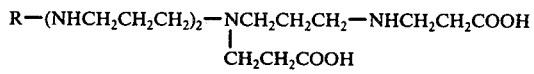

alkyl-tripropylene-tetramino dipropionic acid (POLYAMPHORAM).

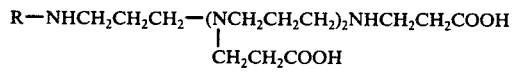

alkyl-tripropylene-tetramino tripropionic acid (POLYAMPHORAM).
R—NHCH₂CH₂NHCH₂CH₂NHCH₂COOH — alkyl-diethylene-triamino acetic acid ("DODICIN").

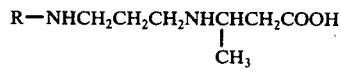

alkyl-propylene-diamino isobutyric acid ("TEGOLAN").

The commercial products are mixtures of compounds of various R having 8 to 18 carbon atoms; that means they are mixtures of compounds the R group of which is mainly octyl, capryl, lauryl, myristyl, cetyl, stearyl, oleyl and linoleyl, while the C₁₂ or C₁₈ groups are generally dominant.

Other usable amino-acids are for example: n-dodecyl-aminoacetic acid, n-tetradecyl-amino-propionic acid, n-hexadecyl-aminoacetic acid, hexadecyl-aminobutyric acid, stearyl-aminoacetic acid, stearyl-aminopropionic acid, oleyl-aminoacetic acid, oleyl-aminopropionic acid, linoleyl-aminoacetic acid, linoleyl-aminobutyric acid, N-dodecyl-ethylenediamino acetic acid, N-dodecylethylenediamino-propionic acid, N-dodecyl-diethylenetriamino-propionic acid, N-oleyl-ethylene diamino-acetic acid, N-stearyl-ethylene diamino-propionic acid, N-linoleyl-ethylene-diamino butyric acid, N-linoleyl-diethylene-triamino-propionic acid, N-dodecyl-bis(ethyl-ethylene)-triamine-acetic acid

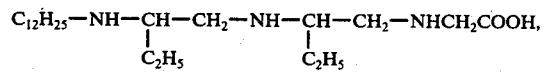

etc. This list being by no means limitative.

The toxicity of such compounds, determined in male and female rats, gives for LD₅₀ values of about 5,000 to 11,000 mg/kg of animal per os. The amino-acids bear the advantage of being even more easily biodegradable than the corresponding amines are.

As concerns the copper compounds, used in the compositions according to the invention, they may be chosen among all known cupric salts of inorganic or organic acids provided the acid be non toxic to plants and animals. Cupric hydroxide may be used advantageously but then care should be taken to bring the pH of the composition to a value near to 7, such as about 6 to about 8.

Thus all the current commercially available Cu salts, such as chloride, nitrate, sulfate, acetate, etc. may be mixed with the amines according to the invention. However, experience proved that to better avoid phytotoxicity and meet the specific sensitiveness of certain vegetals, it is preferable to use copper salts of rather weak acids, such as acetic, propionic, lactic, tartaric, succinic, citric, amino-acetic or similar organic non irritant acids. While it is safer not to use halides, nitrate, nitrite, and even sulfate, copper phosphate, phosphite or phosphonates, as well as borate give good results. Though copper phosphate is insoluble in water, it may be dissolved by complexing with amines, and compositions containing it are very well tolerated by most of plants. Thus the preferred compositions according to the invention contain copper hyroxide or a copper salt of an inorganic or organic acid free from halogen, —NO₂ or —SO₃, and whose ionic dissociation constant does not exceed $2.5 \times 10^{-2}$.

On the other hand, it is recommanded to avoid the use of known toxic anions, as for example, oxalic, cyanic, arsenic, arsenious etc.

While cuprous salts may be used, they are not of much interest as they are oxidized to the corresponding cupric compounds in nature.

It is understood that the compositions of the invention may also contain other heavy metal compounds whether complexed with amine or not. In particular compounds of Zn, Mn or Pb, often used in known fungicides, may be present in the composition. Zinc or/and cadmium can even completely replace copper in the amino complexes of the compositions; however zinc compounds in combination with amines are less active than copper compounds, while the cadmium ones are very expensive. A better solution consists in admixing the other heavy metals compounds with the copper-amine-compositions.

As above mentioned, the addition of certain other compounds to the fungicidal composition can be useful. One particularly efficient class of such additives is that of surface active quaternary ammonium salts. As known, certain such quaternary ammonium compounds have themselves pesticidal properties, as disclosed for instance in U.S. Pat. No. 2,557,172 or by E. C. Hansen and C. A. Bergman in Am. Dyestuff Reptr. July 20, 1953, p. 466. However, they are not usually applied in fields and gardens because generally their action, at sub-phytotoxic doses, is not sufficient. It has been found, when experimenting the present invention, that the addition of surface active quaternary ammonium compounds to the above defined new compositions results in substantially enhancing fungicidal activity, much more than would suggest additivity rule.

Even when the amine is itself surface active, the quaternary compound is generally very useful in improving the spreading and adhering of the composition on the surface of leaves, while enhancing pesticidal action. On the other hand, when water insoluble or not very soluble amines are concerned, the quaternary compound often serves as solvent or dispersant of the amine or copper amine complex. Thus, while quaternary ammonium fungicides alone had no commercial success, they become very useful as additives in the compositions according to the present invention.

Particularly suitable are compounds having the structure

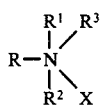

where $R^1$ and $R^2$ are lower alkyls, i.e. $C_1$ to $C_4$ alkyls, more especially methyl and ethyl, R is a heavy alkyl or alkenyl having 8 to 18 carbon atoms, $R^3$ is a $C_1$ to $C_8$ alkyl group which may bear an aryl substituent, X being a monovalent anion. Such compounds are well known, for example by the above cited U.S. Pat. No. 2,557,172 and by U.S. Pat. Nos. 2,700,683 - 2,700,684 - 2,676,986 or 2,691,676. In commercial compounds, X is more often than not a halogen, mainly Cl or Br, the quaternary salt being generally produced by reacting a tertiary amine with a chloro- or bromo-hydrocarbyl.

According to the present invention, while the above halide are suitable, it is more advantageous for the sake of phyto-innocuity and non toxicity to animals to use quaternary ammonium salts in which X is other than halide, nitric, sulfuric or any halide containing anion. Best results are obtained with X being the anion of a rather weak acid the ionic dissociation constant of which preferably does not exceed $2.5 \times 10^{-2}$. Such preferred anions are, for example, acetic, propionic, lactic, salicylic, citric, malonic, succinic, caproic or phosphoric.

The following non limitative examples illustrate the nature of the usable quaternary compounds (the word "ammonium" being replaced by "a."). Octyl-dimethyl-benzyl-a.chloride; decyl-dimethyl-benzyl-a.bromide; oleyl-trimethyl-a.chloride; lauryl-triethyl-a.propionate; stearyl-dimethyl-benzyl-a.bromide; stearyl-dimethyl-ethyl-a.bromide; bis(stearyl-dimethyl-benzyl-a.)sulfate; tris(stearyl-dimethyl-benzyl-a.) phosphate; oleyl-trimethyl-a. lactate; cetyl-diethyl-t.butyl-a.acetate; myristyl-trimethyl-a.caproate; bis(oleyl-dimethyl-benzyl-a.)succinate; lauryl-dimethyl-ethoxycarbonyl-methyl-a. bromide ; lauryl-dimethyl-benzyl-a.saccharinate ; linoleyl-diethyl-hexyl-a. salicylate; linoleyl-dimethyl-benzyl-a. acetate ; tris(lauryl-trimethyl-a.)phosphate; bis(cetyl-trimethyl-a.)maleate etc.

The preparation of the composition according to the invention consists in thoroughly mixing at least one kind of the above defined amine or amine salt with a selected copper compound. The mixture may be carried out with solid, pasty or liquid components. Thus, one manner of preparing the composition resides in grinding together a solid or pasty amine with the required amount of solid copper compound ; that leads to very concentrated compositions, which are pulverulent, granular or pasty, and may then be easily diluted with water by users to give blue solutions or suspensions.

Another process consists in mixing the copper compound with liquid amine or with a solution of the amine. The solutions may be aqueous, alcoholic or hydroalcoholic; while other solvents, when necessary, may be used, such as for example dioxan, tetrahydrofuran, dimethyl-sulfoxide, diethylformamide etc. the most economic way is of course the use of aqueous solutions or dispersions.

Numerous amines and their copper complexes being water soluble, their use is preferred ; this fact eases the preparation and spraying of the composition on fields ; moreover, solutions in general spread better on leaves, diffuse more into the epiderm of the latter and have stronger fungicidal action.

The preparation is generally carried out at room temperature, but it may be useful to somewhat heat the mixture to hasten the dissolution and reaction of the copper compound with the amine. Moderate heating is then preferred ; it is advisable not to reach about 100° C.

As above pointed out, the proportion of amine may vary provided there be 0.1 to 10 aminic nitrogen atoms per Cu atom, and preferably 0.25 to 4 N per Cu. In fact, the proportion depends on the nature of the amine used, on the kind of fungi to combate and on the specie of plant onto which the treatment has to be made. Contrary to prior art, it is not necessary to mix 1 mole of copper compound with 1 or 2 moles of amine, so that all the copper and amine be in the form of complex. According to the invention, it may be advantageous to work with a composition in which there is an excess of non complexed copper salt with respect to the amine, or an excess of non complexed amine over the copper present. Generally an optimum atomic ratio of aminic nitrogen to copper exists for a given fungus and plant, while a good activity can be obtained within the whole above defined range.

A very important factor, particularly as concerns phytotoxicity, is the pH of the composition. While certain plants tolerate somewhat acid or basic liquids, most of them are rather sensitive to pH values beyond the limits of 5.5–8.5 and certain even to pH less than 6 of higher than 8. Then, although pesticide/action is stronger below pH 5.5 and above 8.5, than around pH 7, it is nevertheless safer to adjust the pH of the composition so that, when diluted with water to the concentration of use, its pH be comprised between 5.5 and 8.5, and preferably between 6 and 8. This point has not been considered in the above mentioned prior art ; as numerous of the amines proposed therein have quite strong basic reaction, the copper complex formed often leads to pH higher than 8.5, and exerts a less or more rapid phytotoxic action.

In preparing the composition according to the invention, care is taken that an aqueous solution of 1g of a sample of the product per litre exhibit the above defined pH. When the product is prepared by mixing a copper salt with amine, very often the anion of the salt suffices to bring the pH within the required limits. If not, adjustment is made by adding some acid, such as, for example, acetic, propionic, lactic, phosphonic or other, preferably excluding halogen, $NO_2$ and $SO_3$ containing acids, or some base, at best one of the amines of the invention.

EXAMPLES OF PREPARATION OF THE COMPOSITION

The following non limitative examples will illustrate the invention.

EXAMPLE 1

241 grams (1 mole) of dioctylamine $C_8H_{17}$—NH—$C_8H_{17}$ are ground with 200 g (1 mole) of copper acetate $Cu(CH_3COO)_2.H_2O$. The pasty dark blue material obtained contains 14.3% Cu by weight. It is used for the preparation of a solution by dissolving 5.6g per liter of water. The blue solution obtained has 0.08% Cu and is active again moulds.

EXAMPLE 2

1 mole of N,N'-di-n.hexyl-1,2-diamino ethane $C_6H_{13}$—NH—$CH_2CH_2$—NH—$C_6H_{13}$ (228 g) is ground with 1.5 moles of copper acetate (300g). The mixture has 18.1% Cu. It is used in spraying on plants, against mildew, after dilution of 6 g per liter i.e. to a content of 0.108% Cu.

EXAMPLE 3

A pasty composition is prepared by grinding 1 mole (326 g) of N,N'-di-n.nonyl-1,3-diamine propane $C_9H_{19}$—NH—$CH_2CH_2$—$CH_2NH$—$C_9H_{19}$ with 1.7 moles of cupric formate $Cu(HCO_2)_2$ (260g). The 586 g of product, thus obtained, contains 18.3% Cu. After dilution with water to 0.065% Cu, the composition is efficient in combating moulds on various plants.

EXAMPLE 4

A paste is made by mixing and grinding the following materials :

1 mole (=467g) N,N''-dilauryl-dipropylene triamine, $C_{12}H_{25}$—$NHCH_2CH_2CH_2NHCH_2CH_2CH_2NH$—$C_{12}H_{25}$, 0.7 mole (=140g) copper neutral crystallized acetate, 0.1 mole (=43.5g) copper phosphate $Cu_3(PO_4)_2 \cdot 3H_2O$.

It is used for sprays on plants after dilution with water to a content of 0.0977% Cu, that is 6.5 g of the paste per liter of water. A yet stronger fungicidal is obtained by preparing a similar paste with, in addition, 100g of octyl-dimethyl-benzyl ammonium acetate.

EXAMPLE 5

The method of preceding examples is used to prepare a mixture of :

1 mole (=327g) N,N''-dioctyl-diethylene-triamine, $C_8H_{17}$—$NHCH_2CH_2NHCH_2NH$—$C_8H_{17}$, with 2 moles (=555g) cupric lactate $Cu(C_3H_5O_3)_2 \cdot 2H_2O$.

The material obtained gives good antifungic protection when sprayed onto plants in the form of an aqueous solution having 0.143% Cu.

EXAMPLE 6

Preparation in solution 1 mole(447g) of N,N''-dioctyl-diethylene-triamine diacetate is dissolved in 1 liter of water. 300 ml of an aqueous slurry of $Cu(OH)_2$, containing 72 g Cu, are added to the solution. The mixture is stirred during 6 hours at 27° C and then left to stand for 24 hours. The dark blue solution formed is removed from the remaining deposited copper hydroxide.

The solution has a pH near 8 ; it contains 4.4%Cu, 2% dimethyl-sulfoxide are added thereto, and the solution is diluted 50 times with plain water. A fungicidal solution with 0.088 % Cu is thus obtained, which has excellent action on rose oidium.

EXAMPLE 7

A composition is prepared by adding 177 ml of a $Cu(OH)_2$ slurry containing 22.4 g of combined Cu, to 1 liter of an aqueous solution of :

80 g (=0.245 mol = 0.735 amine equivalent) of N,N''-dioctyl-diethylene triamine, 50 g (=0.114 mol. = 0.342 amine equivalent) of N,N',N''-trioctyl-diethylene triamine 40 g (=0.666 mol = 0.666 acid equivalent) of acetic acid, and 110 g (=0.342 mol) of lauryl-dimethyl-benzyl-ammonium chloride.

The cupric hydroxide progressively dissolves and the solution becomes deep blue. The mixture is stirred during 4 hours at ambient temperature and left to stand for 24 hours ; then the blue solution is separated from the part of deposited hydroxide ; it has 18.9 Cu/liter and shows strong surface activity. pH is adjusted to 7.6 with acetic acid. Diluted with water 45 times, that means to 0.042% Cu, the solution is very efficient in controlling cryptogamic diseases of roses, vine and lilac.

EXAMPLE 8

A composition similar to that of example 7 is prepared, but a fraction of 10g Cu is replaced by 10g of Zn, that means the starting hydroxide is a mixture of $Cu(OH)_2$ with $Zn(OH)_2$. Thus, the activity of the composition against oidium albicans is enhanced.

EXAMPLE 9

89 grams (=0.27 mole = 0.81 amine equivalent + 0.27 acid equivalent) of N-lauryl-diethylene-triamine acetic acid $C_{12}H_{25}$—NH—$CH_2CH_2$—NH—$CH_2CH_2$—NH—$CH_2COOH$ are suspended in 1000 ml of water and 70 g (=0.35 mole) of pulverulent neutral monohydrated cupric acetate are added thereto and stirred during 1 hour.

The dispersion obtained has 22.2g Cu per liter and the atomic ratio N:Cu is 0.81:0.35=2.3.

pH=7. Diluted to 0.1% Cu the composition is surface active and very efficient against moulds.

EXAMPLE 10

In the preparation of example 9, the cupric acetate is replaced by an equivalent amount, i.e. 77g. of zinc acetate, $Zn(CH_3COO)_2 \cdot 2H_2O$.

The composition is still fungicide but milder than that of example 9.

An intermediate very good composition is obtained when using 52g of copper/acetate and 21g zinc acetate instead of the 70 g of Cu acetate of example 9.

EXAMPLE 11

To 578 g of a 50% solution of amino-acids having the structure R—$NHCH_2CH_2COOH$ (AMPHORAM) in a mixture isopropanol-water (50:50), 200 g of crystallized cupric acetate are added together with 60g of N,N'-dihexyl-ethylene diamine $C_6H_{13}$—NH— $CH_2CH_2$—NH—$C_6H_{13}$. The rather viscous mixture is stirred for 2 hours at room temperature and then left to stand. A viscous, homogeneous dark blue liquid is obtained. The amino-acids used are a mixture of several amino-acids the alkyl R of which has 8, 10, 12, 14, 16 and 18 carbon atoms; $C_{12}$ amounts to 56% of the total R, $C_{14}$ to 18% and $C_{16}$ to 10%, while $C_8$, $C_{10}$, $C_{18}$ and $C_{18}$ constitute minor proportions. The average molar weight of the amino-acids used is about 289; the composition has 1 mole of the amino-acids, 0.263 mole of the above diamine (0.526 N atom) for 1 Cu atom; that means 1.526 aminic nitrogen atoms per Cu atom. Due to the addition of the diamine, the pH (after dilution to 1%) of the composition is 6.6.

Diluted to 0.0745% Cu with water, the composition forms a stable suspension, surface active and fungicide, which well wets leaves.

EXAMPLE 12

A cupric complex containing composition is prepared by thorougly mixing 628 g of commercial N-alkyl-amino-propylene-βamino-propionic acid (DIAMPHORAM)

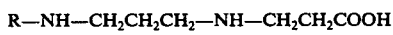

R—NH—CH$_2$CH$_2$CH$_2$—NH—CH$_2$CH$_2$COOH with 200 g of finely ground cupric acetate. The amino-acid is a mixture the different R of which have the same composition as in example 11; it is formed by a 65% solution of the acids in isopropanol-water mixture. The average molecular weight of the amino-acid is 408; thus the atomic ratio of aminic nitrogen to Cu is 2.

All the copper acetate is dissolved and gives a viscous liquid having 7.7% Cu and a very deep blue colour. At 1% dilution in water the pH is 7.5.

Aqueous solutions containing 1% of this material (0.077% Cu) are strongly surface active and kill a great number of moulds.

EXAMPLE 13

In the composition of example 12, the 200g of copper acetate are replaced by a mixture of 100g of copper acetate plus 110g of zinc acetate. The fungicide obtained is milder and its doses should be increased by about 25% but it bears the advantage of cutting by 50% the amount of copper to be brought onto plants.

EXAMPLE 14

Solid N-alkyl-dipropylene-triamino-propionic acids are ground with copper acetate to form a hard paste. The acids are a commercial product constituted by a mixture of several homologous amino-acids differing by their alkyl R, as defined in example 11:

R—NHCH$_2$CH$_2$CH$_2$NHCH$_2$CH$_2$CH$_2$NHCH$_2$CH$_2$COOH the average molar weight of which is 465.

1 mole of the amino-acids is ground with 600 g cupric acetate, that means 1 mole = 3 nitrogen atoms with 3 Cu atoms. The obtained blue material has 17.8% Cu. Diluted with water to 0.08% Cu, it has a pH close to 7, is surface active and fungicide.

Considerable increase in pesticidal activity is obtained by adding, in the course of grinding the starting materials, 120g of tris(stearyl-dimethyl-benzyl-ammonium)-phosphate.

EXAMPLE 15

To 1 kg of cupric acetate, 330 grams of the solid amino-acids of example 14 are added and the mixture is thoroughly ground. The wet powder obtained has 23.8% Cu and 24.8% amino-acid. It is easy to prepare therewith a fungicidal solution by dissolving the powder in water.

15% by weight of oleyl-triethyl-ammonium lactate mixed with the powder strongly enhances the surface activity and fungicidal effect of the material.

EXAMPLE 16

In the preparation of example 15, the cupric acetate is replaced by finely pulverized basic copper carbonate CuCO$_3$ · Cu(OH)$_2$, and to the mixture is added 130 g of lauryl-dimethyl-benzyl-ammonium bromide. The mixture obtained gives with water rather stable blue suspensions which have a fungicidal action similar to that of Bordeaux mixtures, while requiring lower concentrations of Cu than the latter (about 0.2 to 0.8% instead of 1 to 5%).

EXAMPLE 17

A composition is prepared by mixing 108 g (0.1 mol) of a 65% solution in isopropanol-water of N-oleyl-dipropylene-triamine dipropionic acid

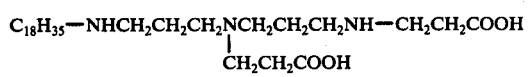

C$_{18}$H$_{35}$—NHCH$_2$CH$_2$CH$_2$NCH$_2$CH$_2$CH$_2$NH—CH$_2$CH$_2$COOH
　　　　　　　　　　　　|
　　　　　　　　　　　CH$_2$CH$_2$COOH with 20 g (0.1 mol) cupric acetate. The mixture is stirred during 1 hour at 50° C. The cupric acetate dissolves and gives a deep blue viscous paste. A fungicidal solution is obtained by diluting the paste 100 times with water.

EXAMPLE 18

356 g of a commercial isopropanol-water solution, which contains 232 g of the amino-acids of example 14, are diluted with 300 g water and added with 100g cupric acetate under stirring. The acetate dissolves in the liquid and gives a dark blue somewhat viscous solution. This constitutes a good fungicidal spray when dissolved in an excess of water to the concentration of about 0.08% Cu. It contains by weight 30.6% amino-acid and 4.2% Cu.

EXAMPLE 19

A composition is prepared with 356 g of the same alkyl-amino-acids solution as in example 18 to which are added 200 g of N,N',N''-trioctyl-diethylene triamine, 160 g of lauryl-dimethyl-benzyl-ammonium bromide, 260 ml of water and 300 g of cupric acetate. After stirring at 25° C until substantially all the acetate is dissolved, the pH of the solution is adjusted with a 10% aqueous phosphoric acid, so as to amount to 6.6 when 1% of the composition is dissolved in water. Diluted to Cu=0.077 the composition exhibits excellent fungicidal action without any phytotoxicity to most of common plants.

EXAMPLE 20

212 g of copper glycinate Cu(NH$_2$CH$_2$COO)$_2$ are dissolved in the mixture of 160 g N,N'-dioctyl-diethylene triamine, 80g N,N',N''-trioctyl-diethylene-triamine, 140g stearyl-dimethyl-benzyl-ammonium acetate and 850 ml water. After 3 hours stirring, the pH of the mixture is adjusted by adding acetic acid until 1% solution of the mixture has pH 7.8. The turbid, blue, viscous composition obtained gives good fungicidal solutions when diluted to about 0.1% Cu.

EXAMPLE 21

To 280 ml of an aqueous solution of cupric acetate, saturated at 20° C (=6.35 g Cu) 120 g of a hydroalcoholic solution are added, which contain 73 g of amino-acids.

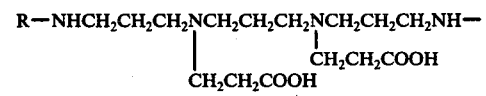

R—NHCH$_2$CH$_2$CH$_2$NCH$_2$CH$_2$CH$_2$NCH$_2$CH$_2$CH$_2$NH—
　　　　　　　　　　|　　　　　　　　　|
　　　　　　　　CH$_2$CH$_2$COOH　　CH$_2$CH$_2$COOH

—CH$_2$CH$_2$COOH

N-alkyl-tripropylene-tripropionic acid; (POLYAMPHORAM) of average molar weight 730; R having the same meaning as in example 11.

The amino-acids dissolve and the blue colour of the solution darkens. Then 20g (=6.35 g Cu) of powdered cupric acetate are added to the solution and they dissolve under stirring. The final solution thus obtained contains 0.2 mole copper/acetate with 0.1 mole alkyl-amino acids.

Diluted to 1% in water it has a pH of 6.2. Sprays of this composition, having 0.07 to 0.14% Cu, are mild fungicides but they are very active when mixed with other amines or amino-acids.

EXAMPLE 22

200 g of solid alkyl-amino-acids having the structure of those of example 21 but the alkyls of which comprise about 28% $C_{18}$, 43% C=18(oleyl) and 28% $C_{16}$ are ground with 120 g of the R—NH—$CH_2CH_2COOH$ amino-acids described in example 11, 180g of N,N''-dilauryl-diethylene-triamine $C_{12}H_{25}$—$NHCH_2CH_2NHCH_2CH_2NH$—$C_{12}H_{25}$, 300 g cupric tartate $CuO_6H_4C_4$ and 200 g zinc tartrate $ZnO_6H_4C_4.2H_2O$. When diluted with water to a 0.06% Cu content the material exhibits excellent antifungic action on plants.

TESTING OF THE COMPOSITIONS

The above described compositions were tested by field experimentation as well as by experience in vitro with various fungi. Phytotoxicity was also determined in greenhouse and in garden. On the other hand, biodegradability has been studied by admixing a typical composition with normal fertile soil.

FIELD EXPERIMENTATION

I. In a garden rose-bushes which were every year strongly attacked by mildew and less strongly by black spot, were divided into 4 groups of 23 bushes each, the same varieties of roses being present in each group (Red Radiance, Michele Meilland, Papa Meilland, New-Yorker, Golden Masterpiece, Madame Herriot, Chrysler Imperial etc).

One of the 4 groups was left from June to October 1973 without any treatment, while the three remaining groups were sprayed every 3 weeks, that means in total 6 times in the course of the above 18 week summer period. When it rained within 24 hours after a spray, this was repeated. The aqueous liquids sprayed were as follows.

A — A suspension of commercial basic copper sulfate wettable powder, having 4,000 ppm Cu.
B — A suspension of a wettable powder of ZINEB i.e. polymer zinc N'N'-ethylene-bis-dithiocarbamate having 2500 ppm of this compound (commercial name "Zinate 80").
C — A solution of the composition according to the Example 7 of the invention, diluted to 440 ppm of Cu and 2560 ppm of amines.

During the 4 months of treatment and observation, it has been noted that A and B stained the leaves of rose so that it was even difficult to well see whether mildew was present or not.

In August, mildew appeared intensely on the lower part of buds while it was very rare on the buds of group C.

Along the whole summer, the leaves of C had their normal sound green colour.

Black spot has been very well controlled in B (zineb treated), little in A (copper) and well in C (Cu + amine).

After the last spray made in the early days of October, it has been observed that as the wettable powders progressively vanished from leaves of A and B, mildew appeared quite rapidly, while its growth on C group's leaves was slow. Thus, before the end of October A and B were strongly invaded while in C mildew became appreciable only after mid-November.

That seems to prove the substances according to the invention are much better absorbed by leaves.

II. Similar experiments were carried out with lilac, oak, vine, pear-tree, mahonia aquifolia, phlox, chrysantemum and pea with the compositions of examples 4, 5, 7, 10, 11, 14 and 19. For comparison usual sprays were made with aqueous suspensions of following commercial fungicides: Karathane, Maneb, Cuprineb and Dichlone. On the other hand, dusting treatments were applied with a powder of cupric hydroxide and sulfur ("Cuprothiol 50"—5% Cu + 50% S).

The most frequent fungi to destroy were: Oidium, Diplocarpon, Monilinia, Botrytis and Coryneum.

It appeared that amino-Cu compositions are as active as the commercial fungicides provided the concentration of solutions sprayed be at least about 1500 ppm of amine and 600 ppm Cu; very good results are obtained with about 2500 ppm amine and 800 to 1200 ppm Cu. That means the amount of Cu required is considerably lower (less than 1/10) than that of usual cupric compositions. While the dosage of amine is equal or somewhat greater than that of usual fungicides, this is compensated by the fact that, contrary to them, the amino-compounds are biodegradable in soil, they do not stain leaves or fruits and are harmless at elevated temperatures (contrary to Karathane, Maneb and Dichlone).

While the amino cupric compositions at above doses have approximately the same activity as the commercial products have versus different fungi, they act much stronger against oidium.

PHYTOTOXICITY

One cannot determine a unique number to define the phytotoxicity of a given substance. Each vegetal has its particular sensitiveness and a substance which is innoxious to one plant may be harmful to another specie. As pointed out at the beginning of the present specification, there are still other factors involved, such as temperature, light, humidity, etc. Now, in order to provide average statistical data which would enable one to make some reasonable comparison between the behaviour of fungicides versus different plants, experiments were carried out with the 20 following species, and the degree of phytotoxicity has been defined as the % of the species having suffered damage from the given substance.

| Wheat | Violet | Vine |
| --- | --- | --- |
| Maize | Tulip | Pear-tree |
| Pea | Phlox | Lilac |
| Soya | Begonia | Spindle-tree |
| Vetch | Chrysanthemum | Hazel-tree |
| Bean | Rose | Oak. |
| Tomato | Erigeron | |

Thus, if a fungicide at certain concentration damages, for example 2 of the 20 species, it is said to have a phytotoxicity of 10%.

The experiments lasted 2 months with one spray every week at temperatures varying between 9° and 31° C, the average daily sunning being of about 4 hours.

The results are set forth in the following Table I. Letter (a) means the concentration which is recommended by producers; (b) is a stronger concentration often applied by users either due to inaccuracy of their work, or because recommended dosage was not efficient.

The meaning of t days in Table I is explained and discussed below in connection with "In vitro tests".

are even not sufficient to well control in field the growth of moulds.

Comparison between No. 2 and 10 shows that the amino-Cu compositions bring about a considerable saving of copper and avoid accumulating it in insoluble form in the soil.

BIODEGRADABILITY

To 10 liters of good and fertile garden soil were added 92 grams of the composition of example 14, that means 40g of N-alkyl-dipropylene-triamino-propionic acid

TABLE I

| No. | Fungicide | Ppm of active substance | | Phytotoxicity % | "t" days |
|---|---|---|---|---|---|
| 1. | Karathane | 250 (a) | | 10 | 5 |
|    | Karathane | 500 (b) | | 30 | 8 |
| 2. | Copper oxychloride | | | | |
|    | Cu | 5000 (a) | | 10 | 3 |
|    | Cu | 8000 (b) | | 20 | 7 |
| 3. | Dichlone | 500 (a) | | 5 | 11 |
|    |  | 1000 (b) | | 30 | 19 |
| 4. | Maneb ("Malineb") | 2000 (a) | | 0 | 10 |
|    |  | 4000 (b) | | 20 | 24 |
| 5. | Captan ("Phytocape") | 1750 (a) | | 0 | 10 |
|    |  | 3500 (b) | | 10 | 25 |
| 6. | N-dodecyl-trimethylene diamino-CuCl$_2$ complex of USP 2,924,551 | 1000 | | 5 | 6 |
|    |  | 2500 | | 35 | 31 |
| 7. | N-dodecyl-trimethylene*-cupric acetate complex (above USP) *diamino | 1000 | | 0 | 4 |
|    |  | 2500 | | 20 | 28 |
| 8. | N-(tetrapropenyl)-diethylene-triamine-cupric nitrate complex of USP 2,977,279 | 1000 | | 0 | 6 |
|    |  | 2000 | | 15 | 24 |
| 9. | N-stearyl-tripropylene-tetramine-cupric chloride complex of French Pat. No. 1,301,904 (example 2) | 1000 | | 5 | 7 |
|    |  | 2000 | | 20 | 27 |
| 10. | Compositions of the present invention: | Amine | Cu | | |
|    | Example 5 | 1600 | 700 | 0 | 17 |
|    |  | 3200 | 1400 | 0 | 38 |
|    | Example 7 | 2200 | 380 | 0 | 28 |
|    |  | 4400 | 760 | 0 | 41 |
|    |  | 6600 | 1140 | 5 | 60 |
|    | Example 9 | 4000 | 1000 | 0 | 29 |
|    |  | 8000 | 2000 | 5 | 48 |
|    | Example 12 | 4950 | 770 | 0 | 39 |
|    | Example 14 | 1960 | 800 | 0 | 17 |
|    |  | 2940 | 1200 | 0 | 34 |
|    | Example 19 | 3500 | 770 | 0 | 46 |
|    |  | 7000 | 1540 | 10 | 72 |

The above statistical results show that, while the compositions of the invention should be used at concentrations (2000 to 4000 ppm) somewhat higher than most of conventional non cupric fungicides are, there is no danger in even considerably exceeding the necessary dose. That means the safety range of these compositions is very broad, while it is rather narrow with known products; the differences between (a) and (b) in No. 1 to 5 are in fact not great, while in No. 10 (invention) phytotoxicity occurs only when an excess of more than 4000 ppm is used.

Inasmuch as the amino-Cu compositions are cheaper than most of conventional fungicides, non toxic and biodegradable there is no inconvenience in using them at stronger concentrations.

Concerning known amino-Cu complexes of No. 6 to 9 it should be noted that substantial phytotoxicity occurs with concentrations between 1000 and 2000 ppm which with 52 g cupric acetate dissolved in 1 liter rain water. The soil was intimately mixed with the solution and then kept at ambient temperature of 15-28° C, outside, under normal light but out of rain, beneath a transparent roof; it was formed into a layer of about 70×70×20 cm (20 cm being its height). From time, to time the layer was sprayed with rain water to preserve its initial humidity.

Every week a sample of 100 ml, cut in approximately the whole height of the layer, was taken out, added with 100 ml water and filtered. Surface tension was measured in the clear filtrate thus obtained. At the start, while the filtrate contained 2000 ppm of the above amino-acid, its surface tension was 36 dynes/cm to air. After 3 weeks it increased to 43 dynes/cm, and continued increasing with time. Finally the 8th weekly determination has shown the tension of 69 dynes, quite close to that of a control made with the starting soil without additive (70.8).

Now it appears that the amino component of the composition has been degraded in soil within 8 weeks.

When Karathane, Maneb, Dichlone or Captan are mixed with a fertile soil in the manner above described, they are still found therein after several months.

IN VITRO TESTINGS

Fungicidal compositions of the above Table I were used in Standard Fungicidal Tests of the American Phytopathological Society with fungi of the species: Monilinia fructicola, Botrytis cinerea, Fusarium oxysporum, Rhizoctonia solani and Plasmopara viticola. It resulted that $LD_{95-100}$ with the aminocupric compositions of the invention required about 200 ppm, with the amine-Cu complexes of cited prior art about 30 ppm and with the conventional fungicides (Maneb, Captan, Dichlone, etc) 10 to 20 ppm. These results do not stand in accordance with field experience and with the advices of producers and literature as concerns the concentrations to be used with conventional fungicides. In fact, on plants no anticryptogamic protection can be obtained with 10 to 20 ppm of Maneb, Zineb or Captane; the concentration really required, as reminded under (a) in the above table, varies between 500 and 2000 ppm, i.e. about 50 to 100 times the standard figure. It is curious to see that with the copper-amine compositions, according to the invention, the concentration required in practice is only 10 to 15 times that of the standard one (2000 to 3000 ppm against 200 ppm). This may be explained by the fact that the Cu-amine compounds are considerably better retained or absorbed by plants; it seems only about 1/50 to 1/100 of a conventional fungicide spray verily acts against pests, while 1/10 to 1/15 of the copper-amine spray is efficient. In other words, the compositions of the invention, while milder than conventional fungicides, are better utilized on the surface of vegetals.

In order to be able to estimate the possible field antifungic effect of a substance from in-vitro tests, the following method has been applied.

Into Petri dishes having 80 mm in diameter, i.e. 50 sq.cm area, and 10 mm dept, a liquid hot agar nutrient solution is poured to form a 5 mm thick layer. The solution contains per liter: 30 g agar-agar, 20 g glucose, 10 g peptone, 0,4 g NaCl and 0.1 g of each of the salts magnesium sulfate, iron sulfate and ammonium phosphate.

After cooling to room temperature and solidification of the nutrient broth, a seed of fungi is sowed on about 5 to 10 sq.mm in the centre of the broth surface. The dishes are then covered with their covers and left in a room with normal day light at the ambient temperature which is noted in each series of tests.

When the fungi developed around the seed over a surface of about 100 to 200 sq.mm (1×1cm to 1.4×1.4cm), that is generally after 1 to 3 days depending on temperature (15° to 25° C), a solution or suspension of the fungicide to be studied is poured onto the whole surface of the broth and allowed to stand in contact with the broth for 5 minutes; then the solution or suspension is removed by inclining by 45° the uncovered Petri dish and then by 90°, until substantially all the liquid has discharged; thus the discharge of liquid sprayed onto leaves, in nature, is simulated, and the amount of the liquid remaining on the surface is only that which wets the surface and adheres thereto. Now the dishes are again covered and left in a room at 15° to 25° C, lighted by daylight.

Of course, in each series of tests there are control dishes, which are treated with boiled water instead of fungicidal solution or suspension.

Every day the Petri dishes are observed and the growing fungi i.e. the area of invaded broth is noted.

Good fungicides stop the development of fungi with respect to that of the controls. However, with usual concentrations of anticryptogamic substance the development is generally only retarded; it continues slowly and the central initial colony progressively spreads around the centre towards the periphery of the dish. Things are just as in nature where because of the shooting again of pests, antifungic treatments must be repeated from time to time.

In the above method a time $t$ is considered, after which a given fungus has spread over the entire surface of the broth (50 sq.cm) in the presence of a given fungicide; best antifungic substances are those with which the time $t$ is as long as possible.

In tests carried out with the above method, the seed was a culture of fungi obtained from rose and vine leaves attacked by parasites, particularly mildew and black spot. The times $t$ in days of complete invading of the Petri dish are given for various substances at different concentrations. The $t$ values find in the last vertical column of above Table I, as concerns known fungicides and certain examples of the invention. On the other hand, the following Table II gives results of similar tests showing a synergistical effect of components according to the invention.

TABLE II

| No. | Fungicide | | Ppm | "t" days |
|---|---|---|---|---|
| 11 | Lauryl-dipropylene-triamino-propionic acid (LDTPA) alone | | 2400 | 8 |
| 12 | N,N"-dioctyl-diethylene-triamine (N,N"DD) alone | | 2400 | 9 |
| 13 | Lauryl-dimethyl-benzyl ammonium chloride (LDBAC) alone | | 2400 | 7 |
| 14 | Cupric acetate (CuAc) alone | | 2400 | 11 |
| 15 | Mixture: LDBAC | 1200 | 2400 | 10 |
|     |          LDTPA | 1200 |      |    |
| 16 | Mixture: LDBAC | 800  | 2400 | 27 |
|     |          LDTPA | 800  |      |    |
|     |          CuAc  | 800  |      |    |
| 17 | Mixture: LDBAC | 1200 | 2400 | 12 |
|     |          N,N"DD | 1200 |      |    |
| 18 | Mixture: LDBAC | 800  | | |

TABLE II-continued

| No. | Fungicide | | | Ppm | "t" days |
|---|---|---|---|---|---|
| | | N,N"DD | 800 | 2400 | 30 |
| | | CuAc | 800 | | |
| 19 | Mixture: | LDBAC | 600 | | |
| | | LDTPA | 600 | 2400 | 37 |
| | | N,N"DD | 600 | | |
| | | CuAc | 600 | | |
| 20 | Mixture: | LDTPA | 1200 | 2400 | 18 |
| | | CuAc | 1200 | | |
| 21 | Mixture: | N,N"DD | 1200 | 2400 | 20 |
| | | CuAc | 1200 | | |
| 22 | Mixture: | bis(stearyl-dimethyl-benzyl-ammonium)-phosphate | 800 | 2400 | 28 |
| | | N,N"DD | 800 | | |
| | | CuAc | 800 | | |
| 23 | Control | | | 0 | 2 |

From the last column of Table I, it can be seen that the duration t of fungicidal effect with copper complexes /no.6 by 10) is longer than that of conventional fungicides (no.1 to 5), when concentrations of 2000 ppm or more are used. The compositions according to the invention (no.10) permit of reaching a very long protection, say 30 to 60 days, because they may be used at concentrations higher than those of known prior substances, without producing damages to plants.

Table II shows an unexpected strong synergistical fungicidal action of amines and amino-acids according to the invention with copper compounds, as well as with quaternary ammonium salts.

I claim:

1. A fungicidal composition comprising a mixture of
   a. at least one amine or amino acid of the formula

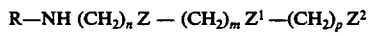
   R—NH $(CH_2)_n$ Z — $(CH_2)_m$ $Z^1$ —$(CH_2)_p$ $Z^2$ wherein R is alkyl or alkenyl of 4-18 carbon atoms; n is 1-6; Z and $Z^1$ are individually — $NHR^1$ or —COOH when monovalent and —NH— or —$NR^1$ when divalent; $Z^2$ is —$NHR^1$ or —COOH; $R^1$ is alkyl of 4-18 carbon atoms, alkenyl of 4-18 carbon atoms or —$(CH_2)_q$— COOH where q is 1-4; m is an integer of 0-6 and $Z^1$ is not present when m is 0; and p is an integer of 0-6 and $Z^2$ is not present when p is 0; said amine or amino acid having at least 8 carbon atoms; and
   b. a cupric salt of a non-toxic acid; wherein the amount of amine is such that there are 0.1-10 aminic nitrogen atoms per Cu atom and wherein at least a part of the copper being combined with the amine in the form of a complex.

2. Composition according to claim 1, wherein n is an integer of 1 to 3 and each of the numbers m and p is an integer of 0 to 3.

3. Composition according to claim 2, wherein one to two of the —$CH_2$— chains bear a branching constituted of a $C_1$ to $C_3$ alkyl.

4. Composition according to claim 2, in which the number of aminic nitrogen atoms per Cu atom is 0.25 to 4.

5. Composition according to claim 1, in which the number of aminic nitrogen atoms per Cu atom is 0.25 to 4.

6. Composition according to claim 1, in which said amine is in the form of a salt of an acid the ionic dissociation constant of which does not exceed $2.5 \times 10^{-2}$.

7. Composition according to claim 1, in which the cupric compound is selected from the group consisting of cupric hydroxide and cupric salts of acids the ionic dissociation constant of which does not exceed $2.5 \times 10^{-2}$.

8. Composition according to claim 5, in which the cupric compound is selected from the group consisting of cupric hydroxide and cupric salts of acids the ionic dissociation constant of which does not exceed $2.5 \times 10^{-2}$.

9. Composition according to claim 6, in which the cupric compound is selected from the group consisting of cupric hydroxide and cupric salts of acids the ionic dissociation constant of which does not exceed $2.5 \times 10^{-2}$.

10. Composition according to claim 1, a 1% aqueous solution of which has a pH of 5.5 to 8.5.

11. Composition according to claim 1, a 1% aqueous solution of which has a pH of 6 to 8.

12. Composition according to claim 1, which contains a quaternary ammonium compound bearing a $C_8$ to $C_{18}$ alkyl or alkenyl on its nitrogen atom, the amount of the quaternary compound being such that there is 0.1 to 1 ammonium nitrogen atom for each aminic nitrogen atom present in the composition.

13. Composition according to claim 12, wherein said quaternary ammonium compound is a salt of an acid the ionic dissociation constant of which does not exceed $2.5 \times 10^{-2}$.

14. Composition according to claim 1 wherein the number of carbon atoms in the R and $R^1$ groups is at least six.

15. Composition according to claim 12 wherein said quaternary ammonium compound is a water soluble salt of the formula

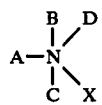

in which A is alkyl or alkenyl of 8 to 18 carbon atoms, B and C are alkyl of 1 to 4 carbon atoms, D is alkyl of 1 to 8 carbon atoms or benzyl, and X is a monovalent anion.

16. Composition according to claim 15 wherein said anion is selected from the group consisting of halide, and the anions of sulphuric, phosphoric, acetic, propionic, lactic, salicylic, citric, malonic, succinic, caproic, maleic, and saccharinic acids.

17. Composition according to claim 16 wherein said anion is that of an acid whose ionic dissociation constant does not exceed $2.5 \times 10^{-2}$.

18. Composition according to claim 12 wherein said amine is selected from a group consisting of N, N'' - dialkyl - diethylene - triamine,
N, N', N'' - trialkyl - diethylene - triamine,
N, N'' - dialkyl - dipropylene - triamine,
N, N', N'' - trialkyl - dipropylene - triamine, in which the said alkyl groups have 8 to 18 carbon atoms; wherein said cupric salt is cupric acetate; and wherein said quaternary ammonium compound is an alkyl-dimethylbenzyl ammonium salt of an acid selected from a group consisting of hydrochloric acid, hydrobromic acid, phosphoric acid and acetic acid, in which the alkyl group has 8 to 18 carbon atoms.

19. Composition according to claim 18 further comprising water in an amount such that the copper is 0.042 to 0.8% by weight of the final composition.

20. Composition according to claim 12 wherein said amino acid is selected from the group consisting of N-alkyl propylene - diamino propionic acid
N-alkyl diethylene - triamino acetic acid
N-alkyl dipropylene - triamino propionic acid
N-alkyl dipropylene - triamino dipropionic acid in which said alkyl group contains 8 to 18 carbon atoms; said cupric salt is cupric acetate; and said quaternary ammonium compound is an alkyl-dimethyl-benzyl ammonium salt of an acid selected from the group consisting of hydrochloric acid, hydrobromic acid, phosphoric acid and acetic acid, in which the alkyl group has 8 to 18 carbon atoms.

21. Composition according to claim 20 further comprising water in an amount such that the amount of copper in the final composition is 0.042 to 0.8 weight percent.

22. Composition according to claim 1 further comprising water in an amount such that the amount of copper in the final composition is 0.042 to 0.8 weight percent.

23. A method of controlling fungi comprising applying to plants a fungicidally effective amount of the composition of claim 1.

24. A method of controlling fungi comprising applying to plants a fungicidably effective amount of the composition of claim 15.

* * * * *